United States Patent
Silipo et al.

(10) Patent No.: US 8,442,620 B2
(45) Date of Patent: May 14, 2013

(54) IMPLANTABLE LEAD/ELECTRODE DELIVERY MEASUREMENT AND FEEDBACK SYSTEM

(75) Inventors: Enzo Silipo, Las Vegas, NV (US); Kyungmoo Ryu, Palmdale, CA (US); Gene A. Bornzin, Simi Valley, CA (US); John W. Poore, South Pasadena, CA (US); Keith Victorine, Sherman Oaks, CA (US); Zoltan Somogyi, Simi Valley, CA (US); Nalin Perera, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 960 days.

(21) Appl. No.: 12/243,674

(22) Filed: Oct. 1, 2008

(65) Prior Publication Data

US 2010/0082087 A1 Apr. 1, 2010

(51) Int. Cl.
*A61B 5/053* (2006.01)
*A61B 5/00* (2006.01)

(52) U.S. Cl.
USPC .......................................................... 600/424

(58) Field of Classification Search .................. 607/115, 607/116, 126–128, 131; 600/377–381, 407; 604/158–170.03
See application file for complete search history.

(56) References Cited

U.S. PATENT DOCUMENTS

| 5,395,328 | A | 3/1995 | Ockuly et al. |
| 5,395,329 | A | 3/1995 | Fleischhackor et al. |
| 5,471,982 | A * | 12/1995 | Edwards et al. ............. 600/374 |
| 5,701,905 | A * | 12/1997 | Esch ............................ 600/486 |
| 5,851,227 | A | 12/1998 | Spehr |
| 5,876,431 | A | 3/1999 | Spehr |
| 5,954,649 | A * | 9/1999 | Chia et al. .................... 600/424 |
| 6,203,493 | B1 * | 3/2001 | Ben-Haim ................... 600/117 |
| 7,072,703 | B2 | 7/2006 | Zhang et al. |
| 7,184,842 | B2 | 2/2007 | Seifert et al. |
| 7,187,982 | B2 | 3/2007 | Seifert et al. |
| 2001/0047134 | A1 * | 11/2001 | Holdaway et al. ............ 600/459 |
| 2004/0088035 | A1 | 5/2004 | Guenst et al. |
| 2004/0127889 | A1 | 7/2004 | Zhang et al. |
| 2004/0243007 | A1 * | 12/2004 | Tenerz et al. ................. 600/486 |
| 2005/0065419 | A1 | 3/2005 | Partridge et al. |
| 2005/0149138 | A1 | 7/2005 | Min et al. |
| 2006/0009831 | A1 | 1/2006 | Lau et al. |
| 2006/0047333 | A1 * | 3/2006 | Tockman et al. ............. 607/127 |

FOREIGN PATENT DOCUMENTS

| EP | 1421913 A1 | 5/2004 |
| EP | 1547648 A1 | 6/2005 |

* cited by examiner

*Primary Examiner* — Carl H Layno
*Assistant Examiner* — Allen Porter, Jr.

(57) ABSTRACT

A lead implantation system with an introducer, a lead configured to engage with the introducer such that the introducer can convey the lead to a desired internal target location, and at least one sensor. The sensor is adapted to generate an indicator of desired engagement of the system with the desired target tissue location prior to engagement of the lead with the target tissue. Also a method of implanting an implantable patient lead including advancing a lead implantation assembly towards a desired target location along an introduction axis and monitoring at least one indicator of lead implantation assembly position along the lead introduction axis. At least one indicator can be generated by the lead implantation assembly. Advancing of the lead introduction assembly can be halted when the monitoring indicates contact with the desired target tissue. The patient lead can then be advanced towards the target tissue and fixed to the target tissue.

20 Claims, 9 Drawing Sheets

IMPLANTABLE LEAD/ELECTRODE DELIVERY MEASUREMENT AND FEEDBACK SYSTEM

CROSS REFERENCE TO RELATED APPLICATIONS

This application contains subject matter that is related to copending U.S. patent application Ser. No. 11/456,825, filed Jul. 11, 2006, titled "Apparatus and Method for Electrode Insertion in Heart Tissue".

FIELD OF THE INVENTION

This invention relates to the field of implantable therapy delivery and/or monitoring systems and to systems and methods of more accurately and reliably performing implantation operations to place structures at desired locations.

BACKGROUND OF THE INVENTION

A variety of medical conditions exist for which ongoing delivery of therapy and/or extended monitoring of the patient's condition is indicated. For example, patients can exhibit medical conditions which indicate extended periods of delivery of therapeutic agents/medications. Patients may also exhibit medical conditions indicating extended stimulation of nerve tissue. Patients may also exhibit a variety of cardiac arrhythmias indicating the ability to monitor the patient's condition and automatically generate and deliver therapeutic stimulations to treat detected arrhythmias. Patients may also exhibit a variety of medical conditions wherein extended monitoring of the patient's physiologic activity can provide valuable diagnostic data to a clinician. However, in general, such information and/or therapy cannot readily or conveniently be obtained/provided via periodic intermittent clinical observations.

In many such circumstances, a clinician can prescribe and arrange for the provision of an appropriate configuration of medical device to provide the indicated therapy and/or monitoring of the patient. Frequently, such medical devices are configured to be at least partially implantable. Implantable structures offer the advantage of extended in situ placement to facilitate delivery of therapy and/or monitoring of physiologic activities at internal locations where access to such locations would otherwise generally require the presence of the patient in a clinical setting and the attention and services of skilled clinical personnel. By providing at least a portion of medical devices in an implantable configuration, the patient is frequently able to at least partially return to a more normal lifestyle while receiving the benefits of therapy delivery and/or diagnostic monitoring at times when they are not in a clinical setting. Implantable devices and structures also offer the advantage to the patient of convenience as the implantable structures are arranged within the patient's body and are not exposed to interference, for example with clothing, and present reduced inconvenience for personal activities such as routine hygiene and physical activity.

Many types of implantable medical devices include lead/electrode structures and/or catheter structures which extend within the patient's body. The lead/electrode or catheter is frequently fixed with respect to patient tissue to facilitate repeatable delivery of indicated therapy and/or measurements of physiologic activity at a desired region of interest. Accordingly, many configurations of implantable devices including patient lead/electrodes and/or catheter structures include provision for fixation to patient tissue. Fixation can be facilitated by sutures, barbs, hooks, and/or a variety of fixation structures.

In a number of implementations, however, there exist difficulties with existing implantable device systems and methods for implantation of such systems in accurately placing and fixing patient leads in desired locations. For example, implantation procedures are frequently performed in a manner such that a fixation location is not easily directly observable by the clinician performing the implantation procedure. Fluoroscopy is one known imaging technique that can be employed by physicians to obtain real-time images of obscured internal structures of a patient and of implantable device structures, including patient leads, to facilitate placement of implantable structures. A fluoroscope generally includes an X-ray source and an imaging screen between which the patient and regions of interest can be arranged. Fluoroscopes can include X-ray image intensifiers and video cameras to facilitate more convenient reviewing and recording of fluoroscope images and to reduce exposure of the patient to ionizing radiation.

One limitation with fluoroscopy however is that it is at least sometimes difficult to accurately discern soft tissue boundaries. This can make it difficult for a clinician to view whether or not an implanted device is at a desired position with respect to target tissue.

Another difficulty with fluoroscopy in positioning of implantable structures is that the obtained image is a two-dimensional image. Thus, while fluoroscopy may be able to relatively accurately provide location information to the clinician in two dimensions orthogonal to the viewing dimension, three-dimensional location information or location information generally along or parallel to the fluoroscopy viewing dimension is less readily discernible. This lack of three-dimensional or "depth" location data can complicate accurate positioning of the implantable structures at the desired location. In addition, as fluoroscopes employ X-ray sources to irradiate the patient tissue and obtain a fluoroscope image, use of fluoroscopy exposes the patient to highly undesirable ionizing radiation. While fluoroscopy can provide highly useful real-time image data, these benefits must be weighed against possible deleterious side effects from exposure to the ionizing radiation.

SUMMARY OF THE INVENTION

Embodiments of the invention provide a lead and lead implantation system and methods of use of a lead system to more effectively position and fix patient leads in desired positions. In general, at least a portion of a lead is configured to be attached or otherwise engaged with patient tissue to restrain unintended further movement of the lead to facilitate maintenance of the lead at the desired location. In various embodiments, a lead fixation structure can be combined with sensing and/or therapy delivery functionality of the lead and in other embodiments lead fixation and therapy delivery and/or sensing are performed by separate structures of the lead. At least certain embodiments include the ability to provide indications or signals of relative engagement of the lead system with patient tissue. In one embodiment, a lead system provides information indicative of relative engagement of the lead system along a direction of engagement or introduction of the lead. In various embodiments, a lead system is adapted to provide signals indicative of one or more of linear translation, pressure, force, and impedance.

One embodiment includes a lead implantation system comprising a lead introducer, a lead configured to engage with the lead introducer such that the lead introducer can convey the lead to a desired internal target tissue location, and at least one sensor wherein the sensor is adapted to generate an indicator of desired engagement of the system with the desired target tissue location prior to engagement of the lead with the target tissue.

Another embodiment includes a method of implanting an implantable patient lead, the method comprising advancing a lead implantation assembly towards a desired target location along an introduction axis, monitoring at least one indicator of lead implantation assembly position along the lead introduction axis, wherein at least one indicator is generated by the lead implantation assembly, halting the advancing of the lead introduction assembly when the monitoring indicates contact with the desired target tissue, advancing a patient lead towards the target tissue, and fixing the patient lead to the target tissue.

A further embodiment includes a system for implanting a lead into internal tissue of a patient, the system comprising a flexible member that defines an interior space and has a distal end wherein an opening is formed in the distal end so as to permit communication between the interior space of the flexible member and a surrounding environment and wherein the flexible member is adapted to be inserted within the body of the patient and moved to a location adjacent the internal tissue of the patient, a lead having a distal end that can be positioned within the interior space of the flexible member wherein the lead is movable with respect to the flexible member so that the distal end of the lead can extend toward a distal end of the flexible member, a first sensor that provides an indication of the relative position of the flexible member with respect to the tissue to thereby allow positioning of the flexible member into a desired orientation with respect to the tissue, and a second sensor that senses the relative orientation of the lead with respect to the flexible member so as to allow the lead to extend out of the opening of the distal end of the flexible member a desired amount so as to contact the tissue. These and other objects and advantages of the invention will become more apparent from the following description taken in conjunction with the accompanying drawings.

DETAILED DESCRIPTION OF THE PREFERRED EMBODIMENT

Figure 1A:
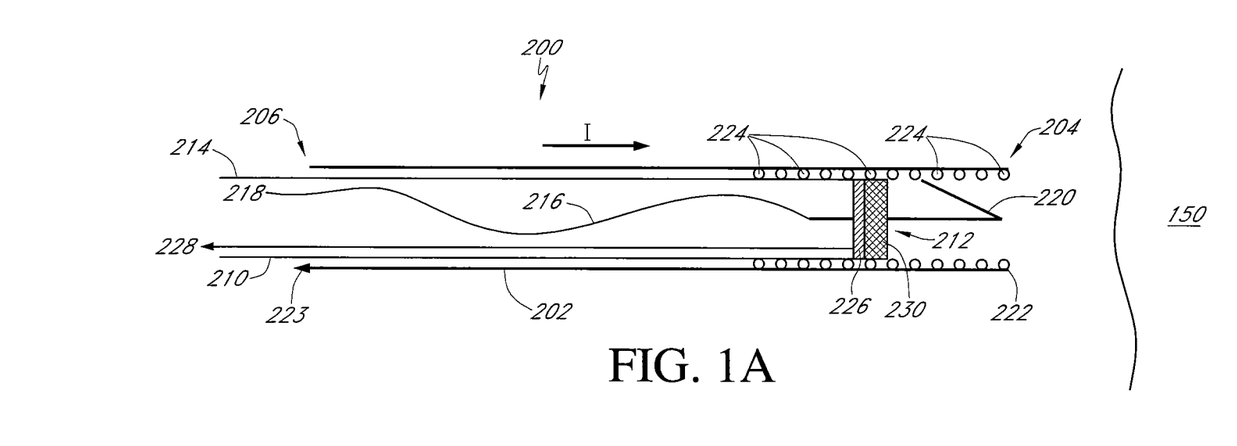
FIG. 1A is a schematic side section illustration of one embodiment of a lead implantation system at an intermediate point in a lead introduction procedure.

FIG. 1 illustrates a schematic side section view of one embodiment of a lead implantation system 200. The lead implantation system 200 is configured to introduce one or more patient leads to a desired implantation location and to facilitate fixation or securing of the patient leads to target tissue 150. In various embodiments, the system 200 can be adapted to implant leads configured solely for delivery of therapy, leads configured solely for sensing or monitoring, and/or leads adapted to perform both delivery of therapy and monitoring and sensing of the patient. In various embodiments, the system 200 can be further adapted to implant leads configured for delivery of therapeutic agents, and/or delivery of therapeutic stimulation. In one particular embodiment, the system 200 is adapted to implant leads configured to provide therapy for one or more cardiac arrhythmias which can include pacing therapy, cardioversion therapy and/or defibrillation therapy.

In one embodiment, the system 200 comprises an introducer 202. The introducer 202 comprises, in one embodiment, an elongate hollow member and can be generally cylindrical in cross section. In certain embodiments, the introducer 202 is semi-rigid to facilitate limited bending during an implantation procedure, for example, to follow natural curves and bends in a transvenous approach. The introducer 202 also has sufficient longitudinal strength that longitudinal force applied along an introduction direction or vector I is sufficiently compressibly resisted by the introducer 202 to allow such force to urge the introducer 202 towards the desired implantation location, e.g., to the target tissue 150.

In this embodiment, the introducer 202 defines a distal end 204 or generally the end of the introducer 202 which will advance towards the target tissue 150 along the introduction direction or vector I. The introducer 202 also defines a proximal end 206 arranged opposite the distal end 204. During an introduction or implantation procedure, force would generally be applied from the proximal end 206 towards the distal end 204 to induce the introducer 202 to the desired location.

It will generally be preferred that the introducer 202 comprises biocompatible materials to reduce undesired deleterious interaction between the introducer 202 and patient tissue through which or along which the introducer 202 may pass. It will also generally be preferred that at least the distal end 204 of the introducer 202 be configured in a relatively smooth outer contour to avoid unwanted abrasion or laceration of patient tissue and to reduce likelihood of the introducer 202 becoming caught or entangled during an implantation procedure.

In at least certain embodiments, the system 200 further comprises a lead forcer 210. A lead forcer 210 will generally define a distal end 212 configured to engage with a distal end of the one or more leads 216. A lead forcer 210 also generally defines a proximal end 214 opposite the distal end 212. In a somewhat analogous manner to the introducer 202, the proximal end 214 of a lead forcer 210 can be configured for manipulation by a clinician to apply appropriate longitudinal and/or rotational force to the lead forcer 210 such that the lead forcer 210 can convey this longitudinal and/or rotational force to the corresponding one or more leads 216.

In at least certain embodiments, the system 200 is further configured to provide signals or other indicia of relative position or location of the system 200 with respect to the target tissue 150. In at least certain embodiments, the system 200 is further configured to provide signals or other indicia of relative location or position of components of the system 200 with respect to other components of the system 200. The sensing or measurement of relative position/orientation between components of the system 200 can include one or both of translational relative position/orientation and rotational position/orientation. These and other aspects and features of various embodiments will be described in greater detail below, including various embodiments of the signals or indicia indicative of position provided by various embodiments of the system 200.

In certain embodiments, a lead forcer 210 is configured as an elongate hollow member. In certain embodiments, a lead forcer 210 is further configured to nest within an interior or lumen of the introducer 202. In at least certain embodiments, the lead forcer 210 has a similar cross-section as the introducer 202 which can comprise a generally cylindrical, ovoid, triangular, square, or other cross-sectional shape appropriate to a particular application.

In certain embodiments, the lead forcer 210 comprises an elongate rod-like member also configured to extend within an interior or lumen of the introducer 202 and to apply force to one or more leads 216 to induce the leads 216 towards the target tissue 150.

In certain embodiments, a lead forcer 210 is configured to apply a generally longitudinal or rectilinear force along an implantation direction or vector I to induce the one or more leads 216 into the desired target tissue 150. In certain embodiments, a lead forcer 210 is configured or adapted to apply rotational forces to one or more leads 216 to induce a turning or rotational movement to the associated one or more leads 216. It will be appreciated that in at least certain embodiments, a lead forcer 210 can be adapted to apply both a longitudinal or rectilinear force as well as a rotational force to corresponding one or more leads 216.

FIG. 1A illustrates one embodiment of a lead implantation system 200 at an intermediate step in an implantation procedure. In this embodiment, the system 200 has been introduced into adjacency with target tissue 150 but the lead 216 has not yet been engaged with or affixed to the target tissue 150, for example, via a fixation structure 220. The fixation structure 220 is generally contoured to facilitate secure attachment to patient tissue. In various implementations the fixation structure can describe a barb, hook, screw or other shape designed to insert directly into patient tissue and self-secure thereto. In other implementations, the fixation structure 220 can describe holes, notches, grooves, or other features to facilitate indirect attachment to tissue, such as via suturing. In certain embodiments, the fixation structure 220 can also be configured for sensing and/or delivery of therapy, for example as an electrode. In this embodiment, the system 200 is configured to facilitate identification of a correct positioning of the system 200 before fixation of one or more leads 216.

In this embodiment, the system 200 comprises an introducer sensor 222 arranged generally at the distal end 204 of the introducer 202. The introducer sensor 222 is configured to provide signals or other indicia 223 as the system 200 proceeds along the introduction or implantation direction or vector I and further configured to provide a signal or other indicia as the introducer 202 engages with the target tissue 150. In one embodiment, the introducer sensor 222 comprises conductive elements and is further adapted to sense a local electrical impedance adjacent the distal end 204 of the introducer 202.

For example, in certain embodiments, the system 200 can be configured to transvenously introduce one or more leads 216 to target tissue 150 comprising cardiac tissue. In these embodiments, as the system 200 is introduced or implanted transvenously, the introducer sensor 222 would sense a generally low local impedance as the system 200 is introduced along a transvenous path where the distal end 204 of the introducer 220 is exposed to blood. As the introducer 202 further proceeds along the introduction or implantation vector I, when the distal end 204 and the introducer sensor 222 of the introducer 202 come into contact with the target tissue 150, for example comprising a region of heart wall, endocardial or epicardial tissue would be expected to exhibit a significantly higher regional impedance than the relatively low bulk impedance blood contacted by the introducer sensor 222 prior to contact with the target tissue 150.

Thus, by monitoring a localized impedance as sensed by the introducer sensor, a clinician or other clinical personnel could observe for periods of relatively low impedance as the system 200 is advanced toward the target tissue 150 and a relatively sharp increase in localized impedance once the distal end 204 engages with the target tissue 150. Thus, in at least certain embodiments, the system 200 is adapted to provide a signal indicative of the longitudinal position or depth of the distal end 204 of the introducer 202. This longitudinal location data can be combined with other data, for example, two-dimensional fluoroscopy images to obtain three-dimensional data indicative of the position of the distal end 204 of the introducer 202 to facilitate more accurate introduction of the system 200 and lead 216 to the desired target tissue 150 in three dimensions.

In at least certain embodiments, the introducer sensor 222 is further configured to confirm that the distal end 204 of the introducer 202 is engaged at a desired location of target tissue 150 prior to engagement or fixation of one or more leads 216. As previously noted, in at least certain embodiments, the system 200 can be adapted for implantation of one or more leads 216 in an implantable cardiac therapy device. The target tissue 150 can comprise a region of cardiac tissue of interest. In these embodiments, the introducer sensor 222 can be configured to test and evaluate capture and thresholds of the introducer 202 as engaged with the target tissue 150.

If the introducer sensor 222 as engaged with target tissue 150 exhibits adequate capture and thresholds, the clinician receives a confirming indication that the system 200 is properly engaged with the desired target tissue 150 and can proceed further with the implantation procedure. If, however, the introducer sensor 222 indicates insufficient capture and/or excessively high thresholds, the clinician receives an indication that perhaps the introducer 202 is not properly engaged with or is misaligned with the desired target tissue 150 and can readjust the system 200 before engaging leads 216.

Thus, embodiments of the system 200 not only provide confirmation that an introducer 202 is properly positioned and engaged with target tissue 150, the system 200 can also indicate to the clinician that the introducer 202 may be mispositioned or inadequately engaged with the target tissue 150 before one or more leads 216 are engaged with the patient tissue. Thus, various embodiments provide a greater degree of confidence to the clinician of appropriate positioning of the introducer 202 as well as reduce the likelihood of the need of removing and repositioning one or more patient leads 216 during an implantation procedure. This provides a more efficient and accurate implantation system 200 for the clinician as well as reduces likelihood of complications for the patient.

In certain embodiments, the system 200 further comprises sensors or other indicia to indicate relative position between the introducer 202 and forcer 210. In one embodiment, the system 200 comprises one or more introducer-forcer sensors 224 and a corresponding forcer sensor 226. In one embodiment, the system 200 comprises a plurality of introducer-forcer sensors 224 that are configured to engage with a forcer sensor 226. In one embodiment, the introducer-forcer sensors 224 comprise one or more conductive rings or contacts arranged on the introducer 202. The forcer sensor 226 also comprises a conductive ring or surface that can engage with one or more respective introducer-forcer sensor(s) 224.

As the lead forcer 210 advances along the introduction or implantation direction I, the forcer sensor 226 can engage successively with one or more introducer-forcer sensors 224 and provide an introducer-forcer position signal 228 indicative of the relative longitudinal position of the lead forcer 210 with respect to the introducer 202. In various embodiments, the introducer-forcer position signal 228 can provide an incremental count as the lead forcer 210 advances along the implantation direction with respect to the introducer 202. In other embodiments, the introducer-forcer position signal 228 is a proportional signal, for example, based on impedance that is indicative of the relative position of the forcer sensor 226 with respect to the introducer-forcer sensors 224. For example different impedance values along different circuit paths can indicate relative position of different components of the system 200. In certain implementations, at least a portion of a circuit can comprise a conductive fluid, such as blood, and an impedance measurement can be based at least in part on the impedance of the fluid portion.

As previously noted, at least certain embodiments of the system 200 provide an indication, such as via the introducer sensor 222, that the introducer 202 is properly engaged with the target tissue 150. The introducer-forcer position signal 228 further provides information indicative of the relative position of the lead forcer 210 as the lead forcer 210 advances to the desired implantation position. Thus, in at least certain embodiments, an appropriate signal or indicia provided by the introducer sensor 222 provides a confirmatory indication to the clinician that the introducer 202 is properly positioned with respect to the target tissue 150. Similarly, an appropriate value of the introducer-forcer position signal 228 provides a confirmatory indication to the clinician that the lead forcer 210 has properly advanced with respect to the introducer 202 towards the target tissue 150. Thus, at least certain embodiments provide additional confirmation indicators to the clinician that both the introducer 202 and the lead forcer 210 have properly extended along the implantation or introduction direction I towards desired engagement with the target tissue 150.

Figure 1B:
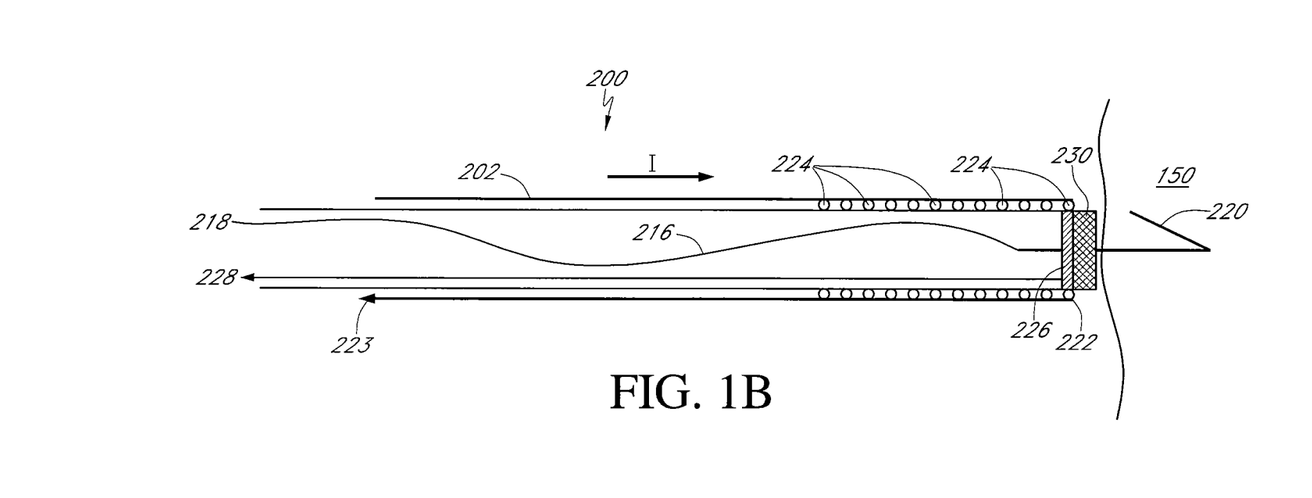
FIG. 1B is a schematic side section illustration of the embodiment of FIG. 1A in a later step of a lead introduction procedure.

At least certain embodiments further comprise a lead stop 230 of the one or more leads 216. In one embodiment, the lead stop 230 comprises a biocompatible flange or disk arranged generally at the distal end of the lead 216. The lead stop 230 is configured to provide a structural obstruction as the lead 216 advances into engagement with the target tissue 150. Thus, in certain embodiments, the lead stop 230 provides a compressive resistance against further advancement of the lead 216. The fixation 220 resists tensile forces on the lead 216 which might otherwise induce the lead 216 to dislodge from engagement with the target tissue 150. Thus, in combination, the lead stop 230 and fixation 220 resist both further introduction of the lead 216 beyond the target tissue 150 and similarly resist withdrawal of the lead 216 from the target tissue 150, for example, under application of tensile force to the lead 216.

Figure 2A:
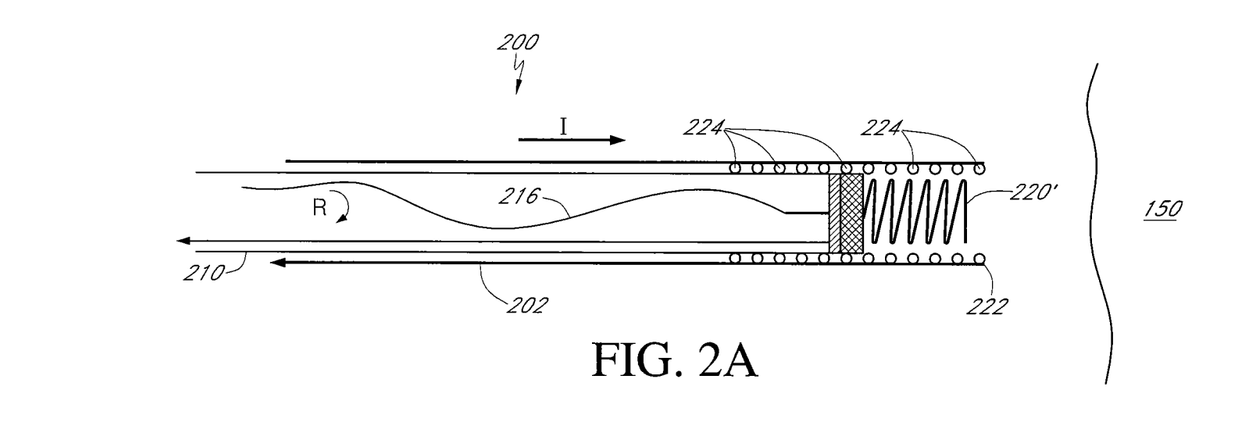
FIG. 2A is schematic side section illustration of another embodiment of a lead implantation system at an intermediate point in a lead introduction procedure.
Figure 2B:
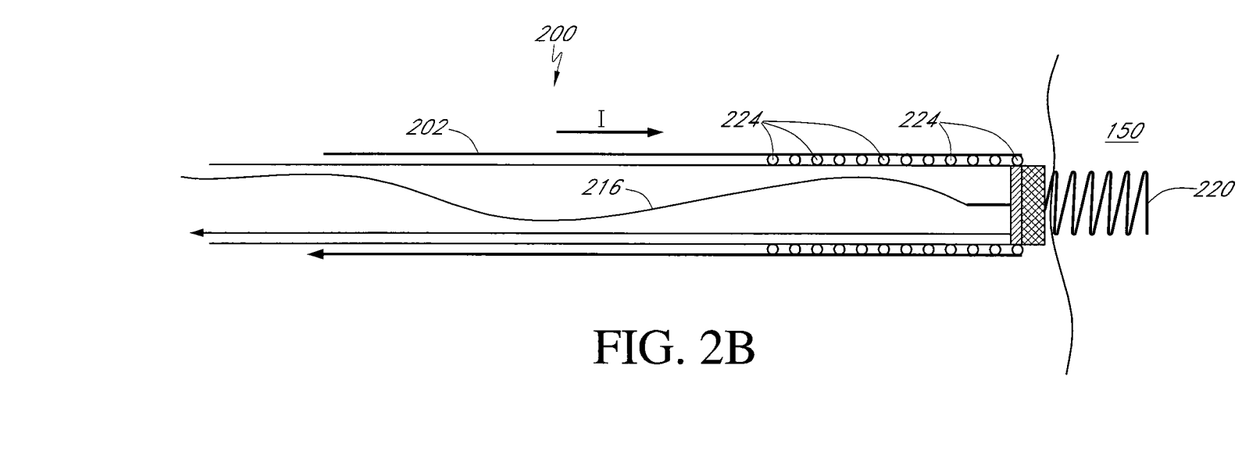
FIG. 2B is schematic side section illustration of the embodiment of FIG. 2A in a later step of a lead introduction procedure.

FIGS. 2A and 2B illustrate embodiments of a lead implantation system that is at least partially similar to the embodiments of lead system 200 previously described with respect to FIGS. 1A and 1B. The embodiments illustrated in FIGS. 2A and 2B differ primarily in the configuration of the fixation indicated in these figures by the designator 220'. The fixation 220 illustrated and described with respect to FIGS. 1A and 1B comprises a barb or hook-type structure to secure the lead 216 in engagement with the target tissue 150.

The fixation 220' of these embodiments is configured generally as a helical or corkscrew configuration. The fixation 220' can be engaged with the target tissue via a combination of longitudinal advancement along the implantation or introduction direction I and a clockwise or counterclockwise rotation of the fixation 220' to thread the fixation 220' into engagement with the target tissue 150 along a generally helical path. The embodiments of lead system 200 illustrated by FIGS. 2A and 2B further differ in that the lead forcer 210 is configured to engage with the lead 216 to apply both longitudinal rectilinear force along the implantation or introduction direction I as well as a corresponding rotation in a clockwise or counterclockwise direction to thread the fixation 220' into engagement with the target tissue 150.

Figure 3A:
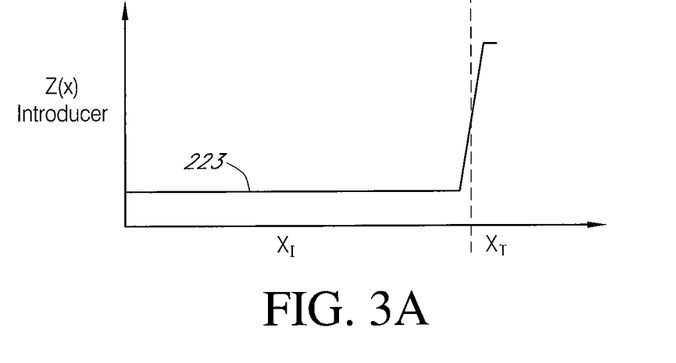
FIG. 3A illustrates an exemplary waveform of a signal sensed by a lead introducer over distance, for example, distance over a lead introduction procedure.
Figure 3B:
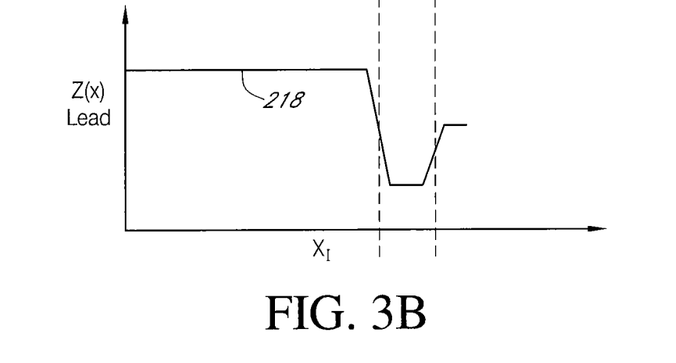
FIG. 3B illustrates an exemplary waveform of signals sensed by a lead over distance, for example, distance over a lead introduction procedure.
Figure 3C:
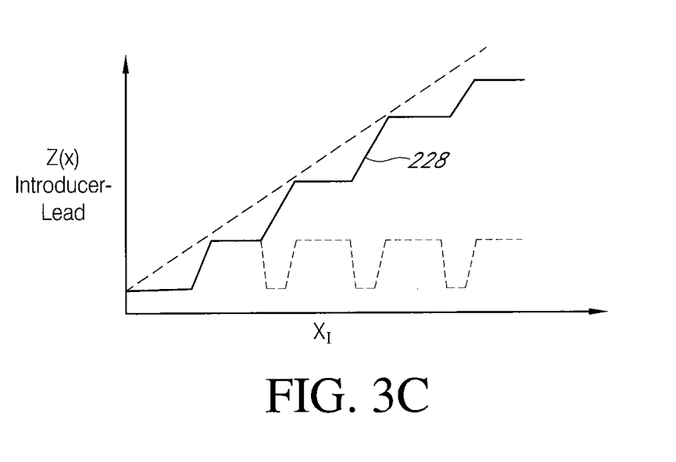
FIG. 3C illustrates a plurality of exemplary waveforms of signals indicating relative position between a lead and a lead introducer over distance, for example, relative movement between a lead and a lead introducer during a lead introduction procedure.

FIGS. 3A, 3B, and 3C illustrate exemplary waveforms of embodiments of a lead implantation system 200 and further illustrating schematically varying signals or indicia provided by the system 200 as the system 200 and various components thereof advance along the implantation direction I and indicated on the horizontal axis of the graphical illustrations as $X_i$.

FIG. 3A illustrates an exemplary waveform of signals or indicia provided by the introducer sensor 222 in embodiments wherein the introducer sensor 222 is configured to sense impedance signals 223. As indicated in FIG. 3A, the introducer sensor 222 would initially sense a relatively low impedance in this embodiment as the distal end 204 of the introducer 202 and the introducer sensor 202 pass through relatively high conductivity, low-bulk impedance blood fluid. As the distal end 204 of the introducer 202 and the introducer sensor 222 engage with the target tissue 150, it would be expected that the introducer sensor 222 sense a significantly higher impedance upon contact with the target tissue 150. This is illustrated in FIG. 3A by the sharp increase in the impedance value at the interface with the target tissue indicated as $X_T$.

FIG. 3B illustrates an exemplary waveform of varying signals or indicia 218 as the lead 216 advances along the introduction direction I, for example, under force applied by the lead forcer 210. The waveform of FIG. 3B can be indicative of signals sensed by the lead 216 itself or alternatively or in combination by one or more sensors engaged with the lead forcer 210, for example the forcer sensor 226. During an initial course of travel, the lead impedance indicated in FIG. 3B as $Z(x)_{lead}$ exhibits a relatively high substantially constant impedance as the lead and lead forcer 210 are in this embodiment at least partially enclosed within the introducer 202 thereby at least partially occluding contact with the relatively low impedance blood fluid. As the lead 216 advances beyond the distal end 204 of the introducer 202, the lead impedance drops as the lead 216 is exposed to ambient relatively low impedance blood fluid. As the lead further advances, the impedance in at least certain implementations would be expected to rise to an intermediate level as the lead 216 and fixation 220 engage with the intermediate impedance of the target tissue 150.

FIG. 3C illustrates embodiments of varying signals or indicia indicative of relative motion between the introducer 202 and the forcer 210, for example, as corresponding to an introducer-forcer position signal 228. In one embodiment, the impedance indicated by the introducer-forcer position signal 228 is step-wise proportional to the relative position between the introducer 202 and the lead forcer 210. In other embodiments, the introducer-forcer position signal 228 provides an approximation of a sawtooth or square wave such that a count can be obtained to determine a relative position between the introducer 202 and the forcer 210. In yet further embodiments, the introducer-forcer position signal 228 can exhibit a substantially continuous linear or otherwise proportional relationship indicative of the relative position between the introducer 202 and the forcer 210.

Figure 4:
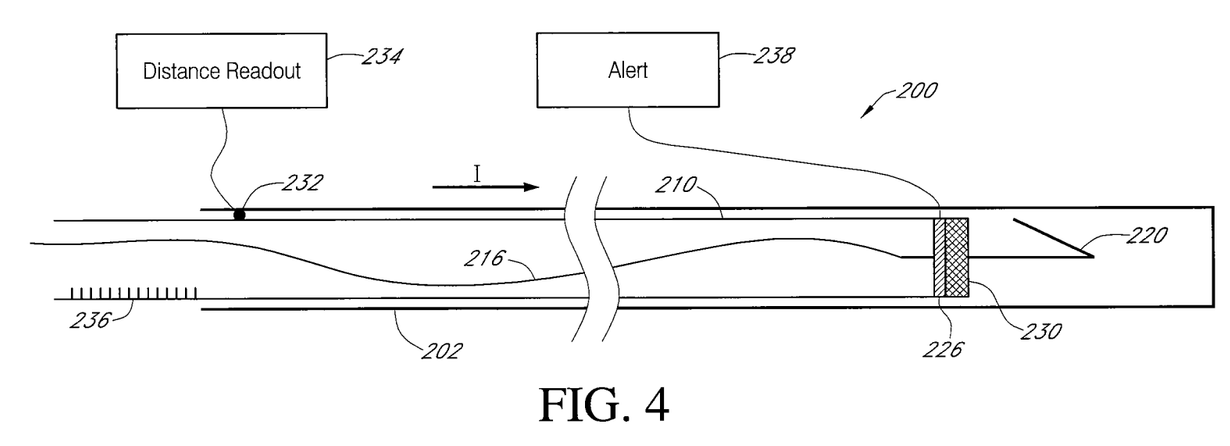
FIG. 4 illustrates a schematic side section view of an embodiment of a lead implantation system including one or more linear translation sensors/indicators.

FIG. 4 illustrates a further embodiment of a lead implantation system 200. In this embodiment, the system 200 includes an introducer 202, a lead forcer 210, and a lead 216. The introducer 202, lead forcer 210, and/or lead 216 can in this embodiment be substantially as previously described for other embodiments of the system, however, in certain implementations may comprise alternative and/or may lack one or more features or structures of the previously described embodiments of the system 200.

In certain embodiments, the system 200 further comprises a linear displacement sensor 232. The linear displacement sensor 232 is configured and arranged to sense linear translation of one or more components of the system, e.g., generally along a lead introduction axis. For example, in certain implementations, the linear displacement sensor 232 is adapted and arranged to sense linear translation of the lead introducer 202 as the lead introducer 202 advances during a lead introduction procedure. In certain implementations, the linear displacement sensor 232 can be configured and arranged to sense relative translation or movement between the lead introducer 202 and the lead forcer 210 and/or between the lead introducer 202 and the lead 216.

In one embodiment, the linear displacement sensor 232 comprises a linear encoder. The linear displacement sensor 232 comprising a linear encoder determines motion by sensing change in position over time. A linear encoder embodiment of the linear displacement sensor 232 can be based on capacitive, inductive, eddy current, magnetic, and/or optical sensing technologies. For example, optically based technologies can include one or more of shadow, self-imaging, and/or interferometric technologies.

In certain preferred embodiments, the system further comprises a linear displacement indicator 234 in communication with the linear displacement sensor 232. The linear displacement indicator 234 is adapted to provide a read out or display of location information provided by the linear displacement sensor 232. In various embodiments, the linear displacement indicator 234 can comprise a separate dedicated indicator providing a digital readout, visual display, and/or other indicator to provide a clinician or other attending personnel information related to the linear position/relationship of the lead implantation system 200 during a lead introduction procedure. In certain embodiments, the linear displacement indicator 234 can be incorporated with other clinical equipment used during an implantation procedure, such as a PSA.

In certain embodiments, the system 200 further comprises a displacement scale 236. The displacement scale 236 generally comprises a plurality of markings or graduations indicating a relative longitudinal and/or rotational position/orientation of one or more components of the system 200, e.g., generally along an implantation axis. In certain embodiments, the displacement scale 236 can comprise calibrated graduations, for example, graduations in an linear inch or metric measurement system. Similarly, in certain embodiments, the displacement scale 236 can comprise calibrated graduations in a rotation measurement system such as degrees, radians, etc. In certain embodiments, the displacement scale 236 can comprise Vernier scale markings. As previously noted, in certain embodiments, the displacement scale 236 can be configured in a similar manner to the linear displacement sensor 232, e.g., adapted to indicate relative position between multiple components of the system 200, such as between the introducer 202 and lead forcer 210 and/or between the introducer 202 and lead 216.

In some embodiments, the system can further comprise one or more alerts 238. The alert 238 is configured to provide an audible, visible, and/or tactile signal to notify a clinician of a determined condition of the system 200. For example, the alert 238 can be configured to generate a distinctive beep or tone, a light, sequence of lights, visual signal, and/or vibrations upon occurrence of one or more selected conditions. For example, in one embodiment, the forcer sensor 226 can be configured to detect contact with the target tissue 150. As previously noted, the forcer sensor 226 can comprise an impedance sensor. In some embodiments, one or both of the introducer sensor 222 and the forcer sensor 226 can comprise force/pressure sensors.

One or both of the introducer sensor 222 and the forcer sensor 226 can be in wired and/or wireless communication with the alert 238. Upon contact with the target tissue 150 one or both of the introducer sensor 222 and the forcer sensor 226 can provide an indication, via the alert 238, that the introducer 202 and/or forcer 210 respectively has made contact with the target tissue 150 based on a change in the sensed characteristic. The alert 238 can provide additional caution against over-penetration of the lead 216 into the target tissue 150. The alert 238 can also be configured to provide a warning notice to the clinician when the forcer 210 gets too close to or passes the distal end 204 of the introducer 202, depending on the particular configuration of the system 200. Thus one or both of the indicator 234 and alert 238 can act as signal generators to provide an indication to the clinician of the relative positional relationships between components of the system 200 with respect to each other and with respect to the target tissue 150.

Figure 5A:
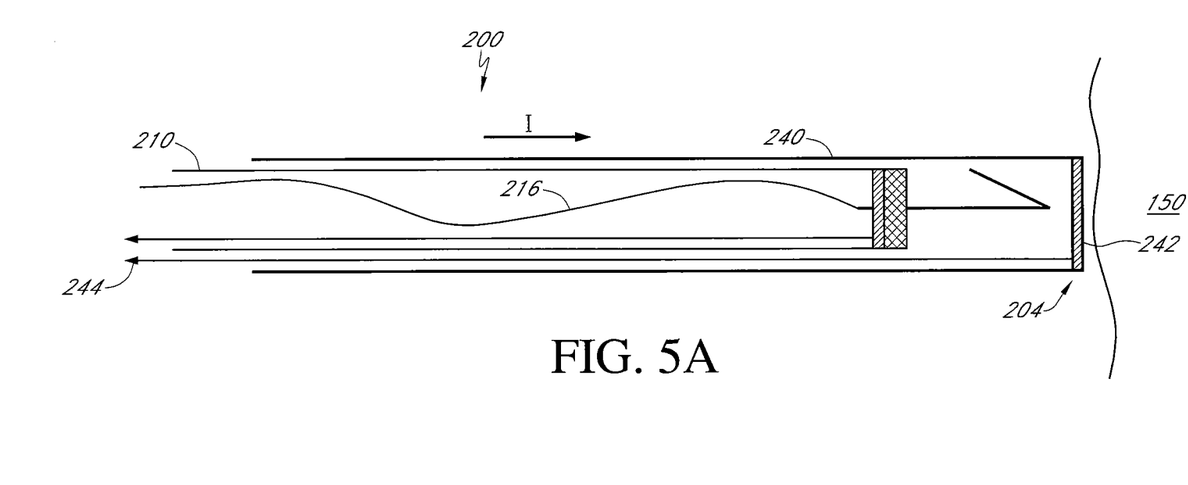
FIG. 5A is another schematic side section illustration of one embodiment of a lead implantation system at an intermediate point in a lead introduction procedure.

FIG. 5A illustrates a schematic side section view of a further embodiment of a lead implantation system 200 in an intermediate step of a lead introduction procedure, e.g., prior to fixation of the lead 216. In this embodiment, an introducer 240 comprises an introducer sensor 242 arranged at a distal end 204 of the introducer 240. The introducer sensor 242 is adapted and arranged to generate and transmit an introducer signal 244 indicating pressure or force acting on the distal end 204 of the introducer 240. For example, during a lead introduction procedure, the introducer sensor 242 would be expected to sense relatively low levels of force or pressure as the system 200 is advanced along a transvenous approach. However, as the distal end 204 of the introducer 240 comes into contact with target tissue 150, the introducer sensor 242 would be expected to sense a marked increase in pressure or force with a corresponding change in the introducer signal 244. Thus, the introducer sensor 242 and introducer signal 244 provide an indication to the clinician when the introducer 240 has advanced and contacted the target tissue 150.

Figure 5B:
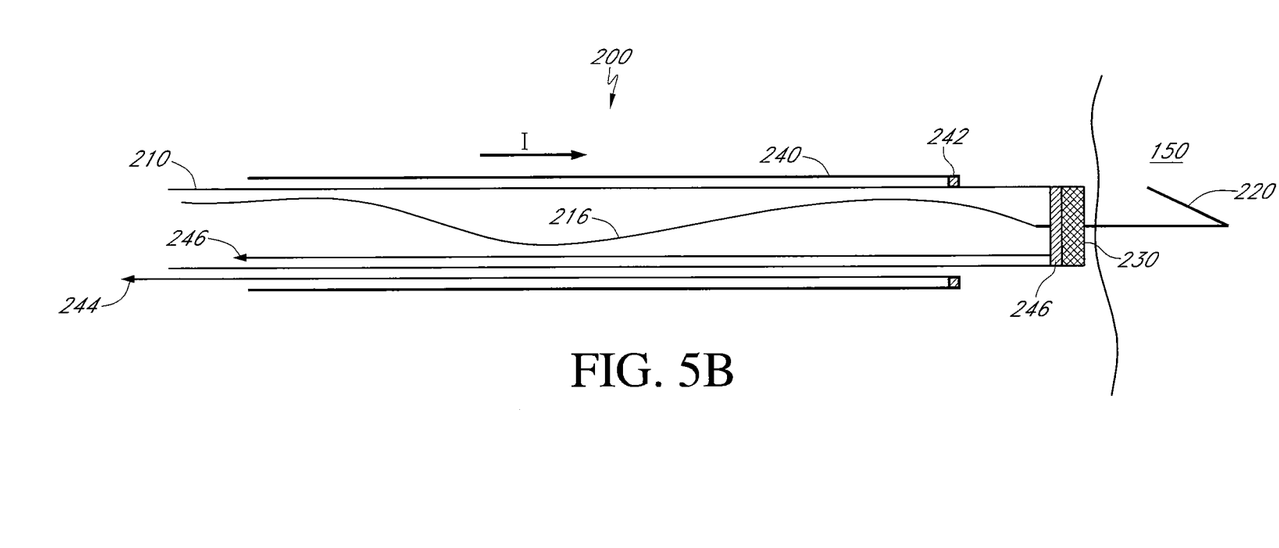
FIG. 5B is another schematic side section illustration of the embodiment of FIG. 5A in a later step of a lead introduction procedure.

FIG. 5B illustrates a schematic side section view of a subsequent or later stage in a lead introduction procedure. In this embodiment, the system 200 comprises a lead sensor 246 arranged generally at a distal end of the lead 216. In certain embodiments, the lead sensor 246 comprises a portion of the lead 216 itself and in other embodiments the lead sensor 246 is associated with a distal end of a lead forcer 210. In either embodiment, the lead sensor 246 is configured to sense pressure and/or force acting on the lead 216 and thereby generate a lead signal 248 indicating the pressure or force sensed by the distal end of the lead 216.

Figure 5C:
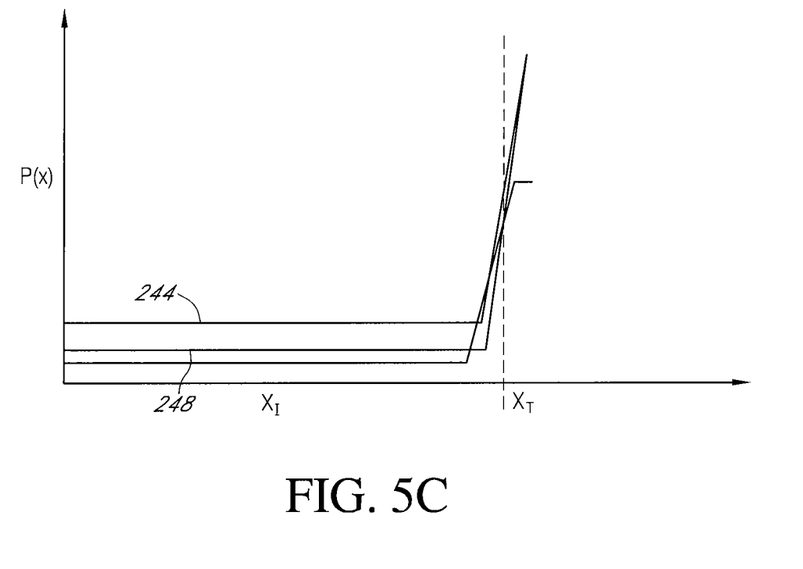
FIG. 5C illustrates an exemplary waveform of signals sensed by a lead implantation system over distance, for example, distance over a lead introduction procedure.

FIG. 5C illustrates exemplary waveforms of the distance relationship of the introducer signal 244 and lead signal 248 during a lead introduction procedure. Over an initial course of travel, both the introducer signal 244 and lead signal 248 exhibit relatively low force or pressure readings as the system advances, for example transvenously, but before contact with the target tissue 150. Upon contact with the target tissue 150 indicated as $X_T$ on the horizontal axis of FIG. 5C, the introducer sensor 242 would be expected to exhibit a marked increase in force or pressure reading as indicated by the steeply increasing value of the introducer signal 244 at the target tissue interface $X_T$. Similarly, as the lead forcer 210 and lead 216 are advanced into engagement with the target tissue 150, the lead sensor 246 and corresponding lead signal 248 would be expected to exhibit a similar sharp increase in force or pressure reading.

It will be understood that while illustrated in FIG. 5C as spatially coincident at the target tissue interface, the temporal increase in the introducer signal 244 and lead signal 248 need not be coincident. For example, in some implementations the introducer 202 is initially advanced into contact with the target tissue followed subsequently by the lead forcer 210 and the lead 216.

As the introducer 240 would generally be removed at conclusion of an introduction procedure, the introducer signal 244 further exhibits a sharp decline to a further relatively low reading as the introducer 240 is withdrawn. In contrast, the lead 216 would be expected to remain in contact with the target tissue 150 as secured by the fixation 220. In at least certain implementations, the lead 216 further comprises a lead stop 230 and thus the distal end of the lead 216 is held in compressive resilient contact with the target tissue 150 between the opposed resisting forces provided by the fixation 220 and the electrode stop 230. Thus, in implementations wherein the lead sensor 246 comprises a distal portion of the lead 216, the lead signal 248 would exhibit an intermediate force or pressure reading due to its compressive engagement with the target tissue 150. It will be understood that in such implementations, while the lead sensor 246 may generate a force or pressure signal, such a lead signal 248 may or may not be further monitored or utilized for the remainder of an implantation procedure, and/or during the implantation period.

Figure 6A:
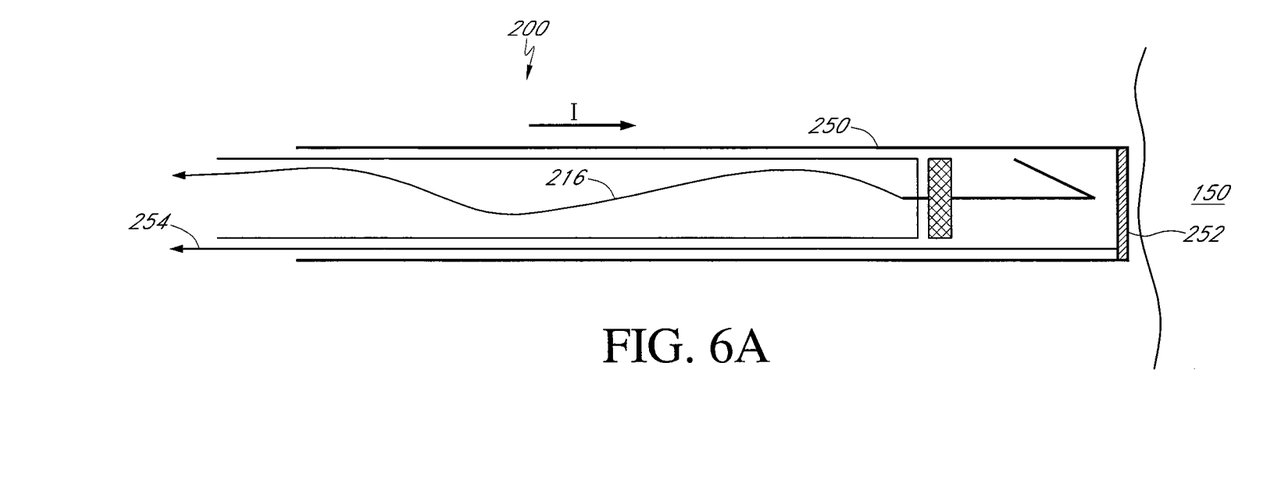
FIG. 6A is another schematic side section illustration of one embodiment of a lead implantation system at an intermediate point in a lead introduction procedure.

FIG. 6A illustrates a schematic side section view of a further embodiment of a lead implantation system 200. In this embodiment, the system 200 comprises an introducer 250 including an introducer sensor 252 arranged at a distal end of the introducer. This embodiment of the introducer 250 can be considered as a simplified embodiment of the introducer 202, for example as illustrated and described with respect to FIG. 1A but lacking certain features of the introducer 202, for example, the introducer-forcer sensors 224 and introducer-forcer position signal 228.

In one embodiment, the introducer 250 comprises an introducer sensor 252 configured to measure an electrical impedance of materials in contact with the introducer sensor 252. In one embodiment, the introducer sensor 252 is configured as a generally annular ring arranged at a distal end of the introducer 250. As the introducer 250 is advanced during a lead introduction procedure, the introducer sensor 252 and a corresponding introducer signal 254 would measure a generally low electrical impedance during transvenous approaches as the blood in contact with the introducer sensor 252 exhibits a relatively low bulk impedance. As the introducer 250 advances into engagement with the target tissue 150, the introducer sensor 252 and corresponding introducer signal 254 would be expected to exhibit a relatively sharp increase as the target tissue 150 would be expected to exhibit a significantly higher electrical impedance characteristic than the relatively low impedance blood. Similarly, as the introducer 250 is withdrawn, the introducer signal 254 would be expected to substantially retrace the signal characteristics exhibited upon introduction of the introducer 250.

Figure 6B:
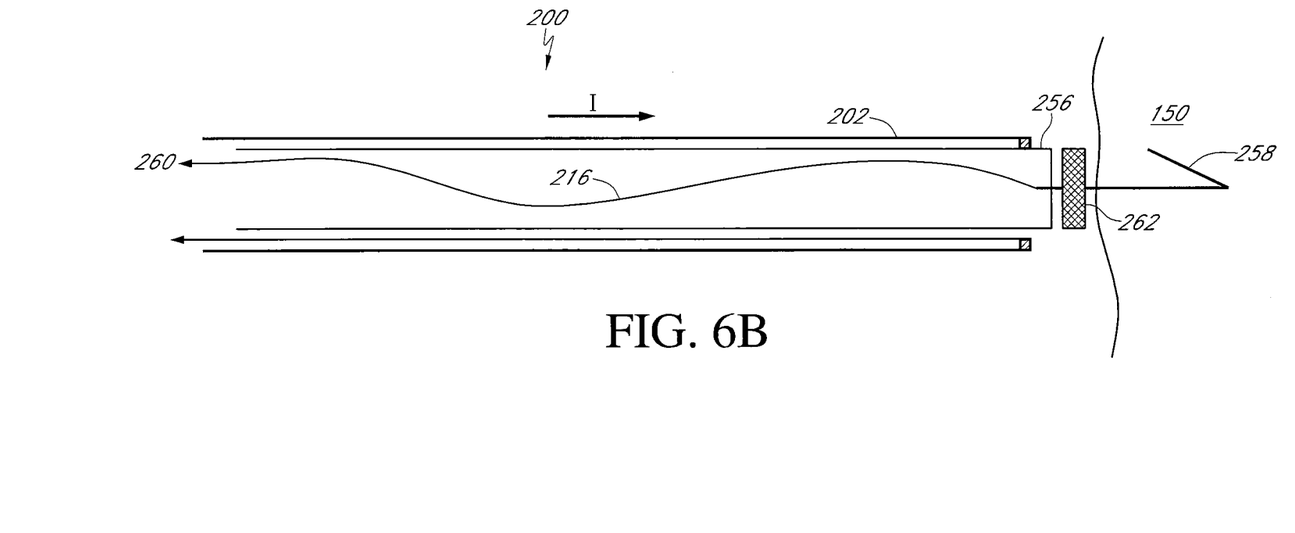
FIG. 6B is another schematic side section illustration of the embodiment of FIG. 5A in a later step of a lead introduction procedure.

In this embodiment, the lead 216 further comprises an electrode 258. The electrode 258 is adapted to provide electrical impedance sensing and in at least certain embodiments is further configured as a fixation structure. In certain embodiments, the lead 216 is configured to reside substantially within the introducer 250 during at least an initial advance towards the target tissue 150. In certain embodiments, the electrode 258 of the lead 216 would be largely isolated from contact with the blood during a transvenous approach and thus a lead signal 260 indicative of lead impedance sensed by the electrode 258 would exhibit a relatively high impedance value during the phase of the lead introduction prior to contact with the target tissue 150. In other embodiments, however, the electrode 258 may also be exposed to contact with the patient's blood and can exhibit a substantially similar lead signal 260 as the introducer signal 254 during the lead introduction procedure.

Figure 6C:
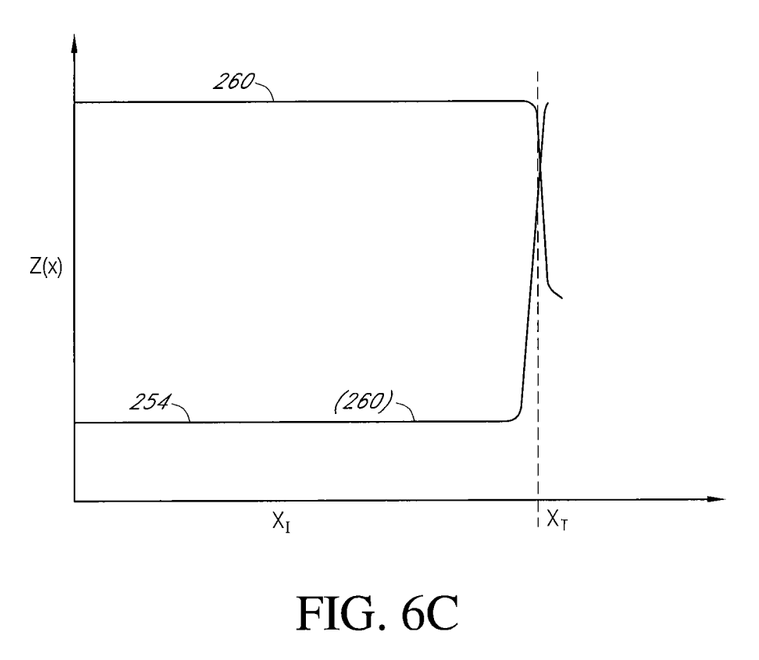
FIG. 6C illustrates an exemplary waveform of signals sensed by a lead implantation system over distance, for example, distance over a lead introduction procedure.

Upon contact with the target tissue 150, the lead signal 260 would be expected to exhibit a substantial reduction or increase upon engagement with the target tissue because the target tissue 150 exhibits an intermediate bulk impedance between the relatively low impedance blood and relatively high impedance air. The lead signal 260 would be expected to continue to exhibit an intermediate impedance reading as the electrode 258 is desirably maintained in contact with the target tissue 150 throughout the implantation period. In certain embodiments, the lead 216 further comprises a lead stop 262 arranged to inhibit further advance of the lead 216 and electrode 258 beyond a desired implantation depth.

Figure 7:
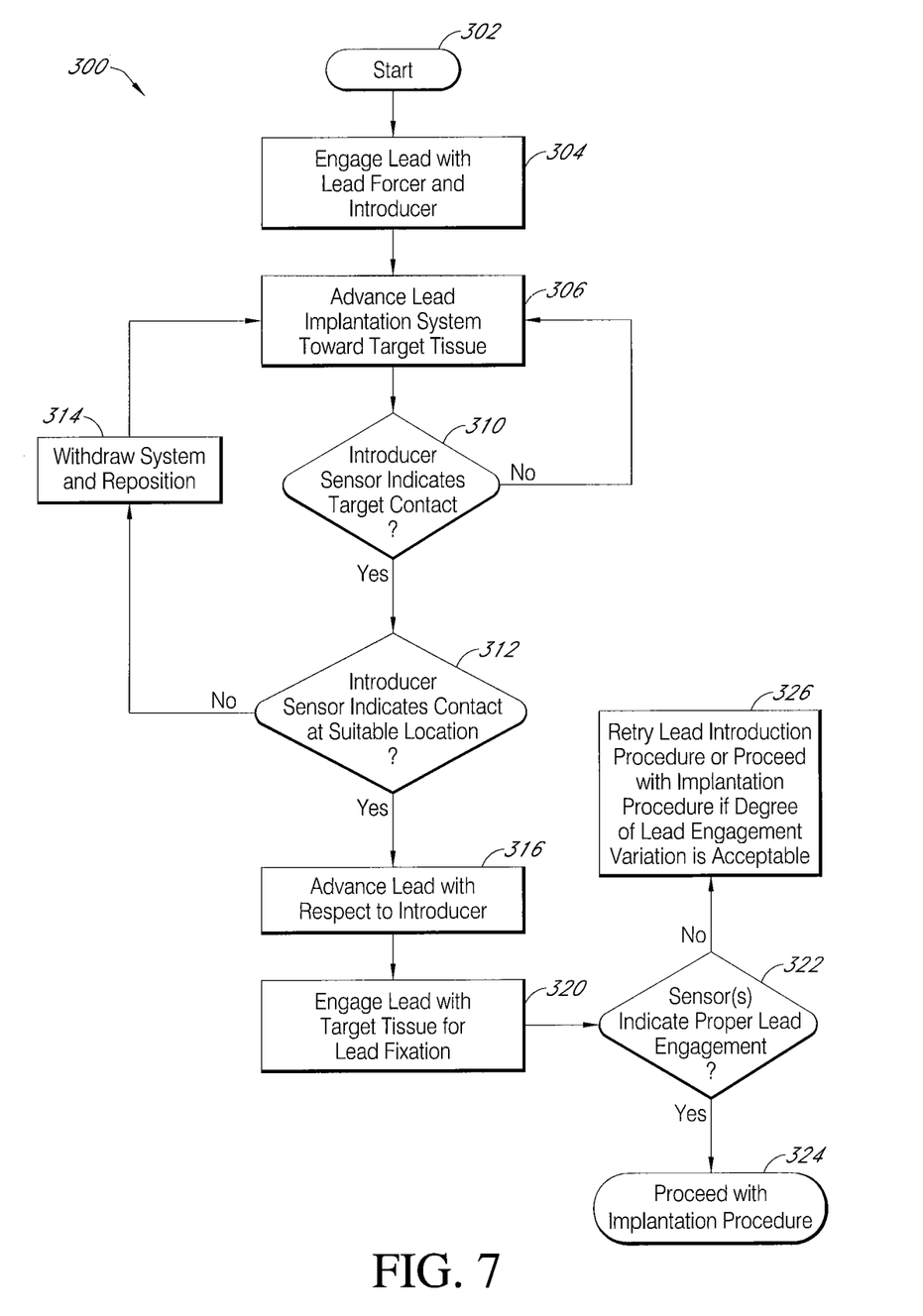
FIG. 7 is a flow chart of embodiments of methods of implanting and implantable lead.

FIG. 7 is a flow chart of embodiments of methods of implanting an implantable patient lead, referred hereafter as method 300 for brevity. The method 300 begins in a start block 302. The start block 302 would generally comprise evaluation of the patient's condition and needs and selection of appropriate therapeutic delivery and/or monitoring systems. The start block 302 would also generally comprise selection of one or more target locations within the patient's body for provision of therapy delivery and/or implanted sensing.

Following from the start block 302 is a block 304 wherein an appropriate patient lead is engaged with a lead forcer and introducer. Following in a block 306, the lead implantation system is advanced towards the corresponding target tissue. Depending on the patient's condition and needs as identified in block 302, block 304 can comprise advancement towards a patient's heart's endocardium and/or epicardium and/or left ventricle transvenous regions.

The method 300 further comprises an evaluation block 310 wherein an evaluation is made whether the introducer sensor indicates proper contact of the system with the target tissue. If the evaluation of block 310 is negative, block 306 continues to proceed by further advancing the system towards the target tissue. When the evaluation of block 310 is affirmative, a second evaluation block 312 can occur wherein an evaluation is made whether the introducer sensor indicates contact at a suitable location.

As previously noted, it is possible that during a lead introduction procedure, such as occurs in block 306, the lead system may advance into contact with patient tissue, however, at a location that would not provide an acceptable quality of performance for therapy delivery and/or sensing of the patient. For example, the introducer sensor 222 can be used to test capture and threshold levels of cardiac stimulation therapy to confirm that the lead system has advanced into contact at an appropriate or suitable location.

If the evaluation of block 312 is negative, a block 314 can occur wherein the system is withdrawn and repositioned and re-advanced in hopes of establishing contact at a desired location. The method 300 offers the advantage, in at least certain aspects, that introduction of the lead system 200 and evaluation of the appropriateness of a contact with target tissue can proceed without engagement of the lead and associated lead fixation structures with the target tissue. These aspects facilitate speed and convenience of implantation for the clinician as well as reduce potential complications and tissue damage for the patient.

If the evaluation of a block 312 is affirmative, a block 316 follows wherein the lead is advanced with respect to the introducer. As previously noted, in various implementations, this can comprise substantially a longitudinal advancement of the lead with respect to the introducer. In at least certain implementations, the block 316 can also include initiation of a measurement process to determine relative position between the lead and the introducer.

Generally at the conclusion of block 316 occurs a block 320 wherein the lead is engaged with the target tissue for lead fixation. In certain implementations, block 320 comprises a rectilinear or longitudinal advancement of the lead such that the lead fixation structure can properly secure the lead to the target tissue. In other implementations, block 320 comprises a combination of longitudinal and rotational movement such that a corkscrew configuration of lead fixation can properly engage with the target tissue.

Following block 320 occurs a block 322 wherein one or more sensors and associated signals are evaluated to determine whether proper lead engagement is indicated. As previously noted, in various embodiments, this can include an evaluation of linear displacement between the introducer and the lead, and evaluation of electrical impedance characteristics exhibited by the lead, an evaluation of pressure and/or force measurements associated with the lead, and/or other measures of confirming the proper engagement of the lead with the target tissue.

If the evaluation of block 322 is affirmative, a block 324 follows wherein remaining blocks of the implantation procedure proceed. It will be understood that in certain implementations, a plurality of patient leads may need to be implanted and evaluated and thus in certain implementations block 324 comprises a repetition or iteration of the method 300. In at least certain implementations, block 324 can further comprise additional evaluations of interface characteristics between the lead and patient tissue, for example, measurement of impedance characteristics, capture, stimulation thresholds, etc. Block 324 can also comprise programming of appropriate therapy delivery and/or measurement parameters depending on the particular characteristics of the individual patient and the implantable device provided.

If, however, the evaluation of block 322 is negative, e.g., that the lead engagement is not proper, a block 326 would generally follow. Block 326 can include a reattempt or retry of the lead introduction procedure and this would generally include manipulation of the lead to withdraw engagement of target tissue and possible replacement of one or more components of the lead system. In certain implementations, even though the evaluation of block 322 indicates improper lead engagement, it can occur that even though lead engagement is not fully proper, the suboptimal lead engagement is sufficient to outweigh risks and potential complications associated with a reattempt at a lead introduction procedure from this point in the preceding introduction procedure. Thus, in at least certain implementations, a clinician may make the professional evaluation that even though block 322 indicates a less than fully desirable lead placement and engagement, the performance will be acceptable. It will be understood that in certain implementations, the programming or adjustment of parameters associated with therapy delivery and/or sensing associated with the lead, for example, thresholds, amplifier gains, stimulation energies, etc., may be adjusted to compensate for any deficit in the engagement of the lead with the target tissue.

Thus, at least certain embodiments of the systems and methods of lead implantation previously described provide the advantage of increased information and convenience to a clinician as well as reducing the likelihood of complications and tissue damage for the patient. More particularly, at least certain embodiments of the system and method provide information indicative of the depth or translation of a lead system along a lead axis that can be utilized with other sensing and/or imaging modalities, such as fluoroscopy to more accurately position a distal end of a lead implantation system in three-dimensional space at a desired target tissue location.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A lead implantation system comprising:
   a lead introducer;
   a lead configured to engage with the lead introducer such that the lead introducer can convey the lead to a desired internal target tissue location; and
   wherein the lead introducer includes at least one pressure sensor adapted to generate a first signal indicating engagement of the lead introducer with the desired target tissue location prior to engagement of the lead with the target tissue and a second signal indicating fixation of the lead with the target tissue.

2. The lead system of claim 1, wherein the lead is adapted to perform at least one of sensing from and delivery of therapeutic stimulation to the target tissue.

3. The lead system of claim 2, wherein the lead is adapted to convey at least one of electrical sensing signals and electrical stimulation signals.

4. The system of claim 1, wherein the at least one pressure sensor comprises a sensor arranged on a distal end of the lead introducer.

5. The system of claim 1, wherein the lead introducer and lead are configured for relative longitudinal movement between the lead introducer and the lead and wherein the at least one pressure sensor provides a signal indicative of a relative longitudinal position of the lead with respect to the lead introducer.

6. The system of claim 1, wherein the lead introducer is configured to engage with the lead to induce at least one of longitudinal advancement of the lead along a lead axis and rotation of the lead about the lead axis.

7. The system of claim 1, further comprising a lead fixation adapted to secure the lead to the desired target tissue location.

8. The system of claim 7, wherein the lead fixation comprises a distal portion of the lead.

9. The system of claim 7, wherein the lead fixation further comprises at least one of a therapy delivery structure of the lead and a sensing structure of the lead.

10. The system of claim 1, further comprising a signal generator to provide a discernable signal to a user indicative of relative positional relationships between at least one of the lead and the lead introducer and between at least one of the lead and the lead introducer and the target tissue.

11. A lead implantation system comprising:
a lead introducer;
a lead configured to engage with the lead introducer such that the lead introducer can convey the lead to a desired internal target tissue location; and
wherein the lead introducer includes at least one impedance sensor adapted to generate a first signal indicating engagement of the lead introducer with the desired target tissue location prior to engagement of the lead with the target tissue and a second signal indicating fixation of the lead with the target tissue.

12. The lead system of claim 11, wherein the lead is adapted to perform at least one of sensing from and delivery of therapeutic stimulation to the target tissue.

13. The lead system of claim 12, wherein the lead is adapted to convey at least one of electrical sensing signals and electrical stimulation signals.

14. The system of claim 11, wherein the at least one impedance sensor comprises a sensor arranged on a distal end of the lead introducer.

15. The system of claim 11, wherein the lead introducer and lead are configured for relative longitudinal movement between the lead introducer and the lead and wherein the at least one impedance sensor provides a signal indicative of a relative longitudinal position of the lead with respect to the lead introducer.

16. The system of claim 11, wherein the lead introducer is configured to engage with the lead to induce at least one of longitudinal advancement of the lead along a lead axis and rotation of the lead about the lead axis.

17. The system of claim 11, further comprising a lead fixation adapted to secure the lead to the desired target tissue location.

18. The system of claim 17, wherein the lead fixation comprises a distal portion of the lead.

19. The system of claim 17, wherein the lead fixation further comprises at least one of a therapy delivery structure of the lead and a sensing structure of the lead.

20. The system of claim 11, further comprising a signal generator to provide a discernible signal to a user indicative of relative positional relationships between at least one of the lead and the lead introducer and between at least one of the lead and the lead introducer and the target tissue.

* * * * *